(12) United States Patent
Stark et al.

(10) Patent No.: US 9,518,184 B2
(45) Date of Patent: Dec. 13, 2016

(54) PROCESS FOR PREPARING BLENDS OF BITUMEN HAVING KNOWN STABILITY PROPERTIES

(71) Applicant: BAKER HUGHES INCORPORATED, Houston, TX (US)

(72) Inventors: Joseph L. Stark, Richmond, TX (US); Ben Morgan, Sugar Land, TX (US); Jennifer D. Draper, Bryan, TX (US)

(73) Assignee: Baker Hughes Incorporated, Houston, TX (US)

( * ) Notice: Subject to any disclaimer, the term of this patent is extended or adjusted under 35 U.S.C. 154(b) by 151 days.

(21) Appl. No.: 14/596,864

(22) Filed: Jan. 14, 2015

(65) Prior Publication Data

US 2015/0126647 A1    May 7, 2015

Related U.S. Application Data

(63) Continuation-in-part of application No. 13/738,537, filed on Jan. 10, 2013, now abandoned.

(60) Provisional application No. 61/586,090, filed on Jan. 12, 2012.

(51) Int. Cl.
*C08L 95/00*     (2006.01)
*G01N 31/16*    (2006.01)
*G01N 21/25*    (2006.01)

(52) U.S. Cl.
CPC ............. *C08L 95/00* (2013.01); *G01N 31/162* (2013.01); *C08L 2205/02* (2013.01); *C08L 2555/10* (2013.01); *C08L 2555/34* (2013.01); *C08L 2555/80* (2013.01); *G01N 21/25* (2013.01)

(58) Field of Classification Search
None
See application file for complete search history.

(56) References Cited

U.S. PATENT DOCUMENTS

| | | |
|---|---|---|
| 8,017,910 B2 | 9/2011 | Sharpe |
| 2011/0278460 A1 | 11/2011 | Respini |
| 2012/0125087 A1 | 5/2012 | Sandu et al. |
| 2013/0310492 A1 | 11/2013 | Morgan et al. |

FOREIGN PATENT DOCUMENTS

WO    WO 2013130930 A1 *    9/2013    ............. G01N 31/16

* cited by examiner

*Primary Examiner* — Randy Gulakowski
*Assistant Examiner* — Christopher M Rodd
(74) *Attorney, Agent, or Firm* — Mossman, Kumar & Tyler, PC

(57) ABSTRACT

Bitumen may be prepared by obtaining an inflection point value for a mixed bitumen product stream sample, and modifying the mixed bitumen product stream when the inflection point value occurs at a ratio of less than about 2 mL of added non-solvent per 1 gram of the mixed bitumen product stream sample. The inflection point value may correlate to the stability of the mixed bitumen product stream based on the amount of added non-solvent. The mixed bitumen product stream may have or include at least two bitumen feed streams.

18 Claims, 1 Drawing Sheet

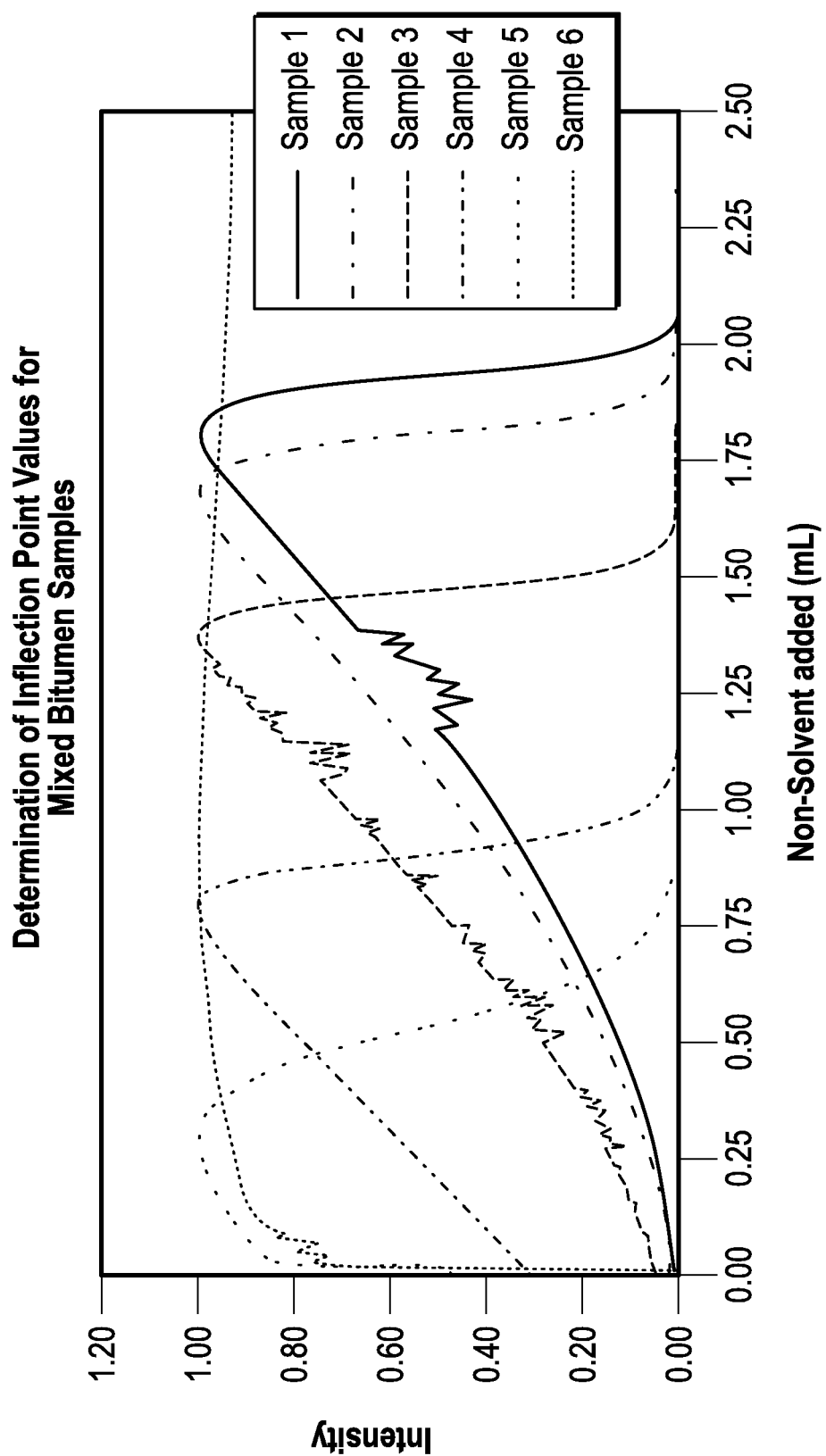

PROCESS FOR PREPARING BLENDS OF BITUMEN HAVING KNOWN STABILITY PROPERTIES

CROSS-REFERENCE TO RELATED APPLICATIONS

This application is a Continuation-in-Part and claims priority from U.S. application Ser. No. 13/738,537 filed on Jan. 10, 2013; which claims priority from U.S. Provisional Application Ser. No. 61/586,090 filed Jan. 12, 2012; both of which are incorporated herein by reference in its entirety.

BACKGROUND OF THE APPLICATION

1. Field of the Invention

This invention relates to manufacturing and using bitumen to produce products such as road paving. This invention particularly relates to blending bitumen for use in road paving applications.

2. Background of the Prior Art

Very heavy hydrocarbons are generally referred to in the art as bitumen, kerogen, asphalt, and tar. These materials may be the high molecular weight hydrocarbons frequently encountered in subterranean formations. They may also be the similar materials resulting from refining crude oil. These very heavy hydrocarbons range from thick viscous liquids to solids at ambient temperatures.

When produced directly from geological formations, they are generally quite expensive to recover in useful form. For example, bitumen occurs naturally in tar sands in locations such as Alberta, Canada and in the Orinoco oil belt north of the Orinoco river in Venezuela. Kerogens are the precursors to fossil fuels, and are also the material that forms oil shales. Kerogens are frequently found in sedimentary rock formations. Asphalts or bitumen is also the term applied to the very heavy hydrocarbons resulting from crude oil refining steps such as cracking and coking.

Bitumen is a long lasting material, even in severe environments, and can almost always be recycled. Sources of recycled bitumen include, but are not limited to, road asphalt, automobile tires, roofing shingles, and roofing membranes. In recycling bitumen, it is often desirable to mix a recycled bitumen stream with a virgin bitumen stream. Sometimes, a heavy hydrocarbon that not necessarily an asphalt or bitumen may be used to mix with the recycle stream.

Unfortunately, these bitumen streams are not always compatible which can lead to premature failure of the bitumen product produced therewith. It is difficult to predict which bitumen mixtures are compatible and which are not so it would be desirable in the art to be able to reliably determine the stability of bitumen product streams prior to using those streams to manufacture products such as road paving materials.

SUMMARY OF THE INVENTION

There is provided, in one form, a method for preparing bitumen by obtaining at least one inflection point value for a mixed bitumen product stream sample, and modifying the mixed bitumen product stream when the inflection point value occurs at a ratio of less than about 2 mL of added non-solvent per 1 gram of the mixed bitumen product stream sample. The inflection point value may correlate to the stability of the mixed bitumen product stream based on the amount of added non-solvent to the mixed bitumen product stream sample. The mixed bitumen product stream may have or include at least two bitumen feed streams.

There is provided, in a non-limiting form, a method of preparing bitumen by obtaining an inflection point value for a mixed bitumen product stream sample, and introducing at least one stabilizing additive into the mixed bitumen product stream when the inflection point value occurs at a ratio of less than about 2 mL of added non-solvent per 1 gram of the mixed bitumen product stream sample. The mixed bitumen product stream may have or include at least two bitumen feed streams. The inflection point value may be obtained adding a non-solvent to the mixed bitumen product stream sample, transmitting near IR laser light through the mixed bitumen product stream sample, and determining that inflection point value that correlates to the stability of the mixed bitumen product stream based on the amount of non-solvent added.

There is further provided in an alternative non-limiting embodiment of a method of preparing bitumen by obtaining an equilibrated mixed bitumen product stream sample comprising at least two bitumen feed streams, analyzing the stability of the equilibrated mixed bitumen product stream to obtain an inflection point value, and modifying the equilibrated mixed bitumen product stream when the inflection point value occurs at a ratio of less than about 2 mL of added non-solvent per 1 gram of the equilibrated mixed bitumen product stream sample. Analyzing the stability of the mixed bitumen product stream may occur by adding a non-solvent to the equilibrated mixed bitumen product stream sample, transmitting near IR laser light through the equilibrated mixed bitumen product stream sample, and determining the inflection point value. The inflection point value may correlate to the stability of the mixed bitumen product stream based on the amount of added non-solvent to the mixed bitumen product stream sample.

BRIEF DESCRIPTION OF THE DRAWING

FIG. 1 is a graph of the measured transmittance values per amount of non-solvent added to samples 1-6.

DETAILED DESCRIPTION OF THE INVENTION

It has been discovered that the stability of mixed bitumen product streams may be analyzed by obtaining an inflection point value for a mixed bitumen product stream sample. The inflection point value may correlate to the stability of any asphaltenes present in the mixed bitumen product stream based on the amount of added non-solvent to the mixed bitumen product stream sample. The mixed bitumen product stream may have or include at least two bitumen feed streams. The inflection point value may be obtained adding a non-solvent to the mixed bitumen product stream sample, transmitting near IR laser light through the mixed bitumen product stream sample, and determining that inflection point value that correlates to the stability of the mixed bitumen product stream based on the amount of non-solvent added.

The mixed bitumen product stream may be modified when the inflection point value occurs at a ratio of less than about 2 mL of added non-solvent per 1 gram of the mixed bitumen product stream sample. In a non-limiting embodiment, the mixed bitumen product stream may be modified when the ratio is less than about 1.2 mL of added non-solvent per 1 gram of the mixed bitumen product stream sample.

The modifying of the mixed bitumen product stream may occur by a method, such as but not limited to, altering the ratio of the bitumen feed streams within the mixed bitumen product stream, introducing at least one stabilizing additive to the mixed bitumen product stream, and combinations thereof. In a non-limiting embodiment, the modifying of the mixed bitumen product stream may occur by introducing at least one stabilizing additive to the mixed bitumen product stream, and the mixed bitumen stream having the stabilizing additive(s) may be analyzed to determine an inflection point value thereof.

In a non-limiting example, the inflection point value may be conveyed in a graph, a report, combinations thereof, and the like. The mixed bitumen product stream may be analyzed to obtain the inflection point value thereof. The analysis of the mixed bitumen product stream may include adding non-solvent to an equilibrated mixed bitumen product stream sample, transmitting near IR laser light through the equilibrated mixed bitumen product stream sample, and determining an inflection point value. The non-solvent has a high enough boiling point that the non-solvent would not boil out of the sample being measured in a non-limiting embodiment. Non-limiting embodiments of the non-solvent may be or include n-alkanes having at least 5 carbons (i.e. n-pentane). In a non-limiting embodiment, the n-alkane may be or include, but not limited to n-pentane, n-heptane, n-hexadecane, and combinations thereof.

A bitumen may be not be viscous for a transmittance detector to detect changes in the transmittance thereof when adding a non-solvent thereto, such as a semi-solid or solid bitumen sample. To accommodate a less viscous bitumen sample, the sample may be optionally heated and allowed to equilibrate prior to analyzing the mixed bitumen product stream to obtain the inflection point value. The sample does not have to be heated; however, heating the sample may allow the sample to be more flowable (less viscous) and easier for a transmittance detector to detect the transmittance of the mixed bitumen product stream. In a non-limiting embodiment, the transmittance detector may be a photo diode having a laser light in the near infrared region at 50 nanowatt (nW) to about 40 milliwatt (mW).

Point of equilibrium' or 'equilibrated sample' refers to the point at which the asphaltenes are stable within the mixed product stream sample, i.e. there is no flocculation by the asphaltenes within the mixed bitumen product sample. Said differently, the 'point of equilibrium' is the point where the transmittance is the highest for a particular mixed bitumen product stream sample, assuming the temperature and viscosity remain the same during all of the transmittance measurements of the sample. The 'point of equilibrium' may change depending on the temperature, viscosity, or other rheological properties of the sample. For example, two bitumen samples may be analyzed that are of the same bitumen stream. The transmittance of one bitumen sample may be measured at room temperature, but the other bitumen sample is measured at 50 C; the inflection point value for such hypothetical bitumen samples would be different because a physical parameter related to the sample has changed, even though the chemical composition remains the same.

A non-solvent, such as a viscosity reducing agent n-butane, may be added, and the near laser transmittance may be monitored. When asphaltenes begin to flocculate, the laser transmittance may decrease. The near infrared transmittance data obtained from the mixed bitumen product stream may be plotted on a graph vs. volume of non-solvent added. Such data may be a relative measure of the point of flocculation.

The inflection point value may be the value representative of the amount of non-solvent required to cause the asphaltenes in the bitumen to become unstable and precipitate. The inflection point value is simply used as a marker to determine stability properties of the asphaltenes based on the amount of non-solvent added at the point of asphaltene flocculation. The amount of non-solvent added to the mixed bitumen product stream may be graphed to determine the inflection point value. The inflection point value is simply the point represented by maximum transmittance on a graph where the amount of non-solvent added is labeled on the x-axis of the graph, and the transmittance values obtained from shining a near infrared laser through the mixed bitumen product stream sample is labeled on the y-axis of the graph. The transmittance of the mixed bitumen product stream may initially increase when titrating the sample with the non-solvent because the mixed bitumen product stream sample is being diluted, but asphaltenes may have not yet precipitated. The laser may shine through the diluted sample easier, so the transmittance initially increases.

As mentioned, the laser may have a wavelength in the near infrared range, such as but not limited to 700 nanometer (nm) independently to about 2500 nm, alternatively from about 1000 nm independently to about 1800 nm in another non-limiting embodiment. As used herein with respect to a range, "independently" means that any threshold may be used together with another threshold to give a suitable alternative range, e.g. about 700 nm independently to about 1800 nm is also considered a suitable alternative range.

After enough of the non-solvent has been added to the mixed bitumen product stream to destabilize the asphaltenes therein, and the asphaltenes may begin precipitating out of the mixed bitumen product stream. The precipitated asphaltenes decrease the ability of the laser to shine through the sample, which results in a decrease in transmittance measurements thereafter. The volume of added non-solvent at the point of inflection where transmittance starts to decrease is the inflection point value.

The final amount of non-solvent added to the mixed bitumen product stream depends on the point at which the asphaltenes begin to flocculate or become unstable; said differently, the final amount of added non-solvent will vary for each mixed bitumen product stream sample depending on the amount and stability of the asphaltenes present therein. The inflection point value allows for a correlation to be drawn from the amount of added non-solvent to the mixed bitumen product stream sample at the time the asphaltenes begin to flocculate within the mixed bitumen product stream.

Obtaining the inflection point value for each blend may allow for comparison of two or more mixed bitumen product streams, as well as the stability of a particular mixed bitumen product stream. Mixed bitumen product streams that require small amounts of non-solvent to reach the inflection point value may be unstable; such instability may create operational problems due to asphaltene precipitation therein. Mixed bitumen product streams that require large volumes of non-solvent to reach their inflection point values are more stable and cause little problems in crude oil blending operations. Basically, the addition of more non-solvent required for the mixed bitumen product stream to reach its inflection point value, the more stable that particular mixed bitumen product stream is.

Also worth noting here, individual bitumen streams may be analyzed for an inflection point value in the same manner as discussed for the mixed bitumen product streams. Incorporating stable individual bitumen streams into a mixed bitumen product streams may result in stable mixed bitumen product streams.

To form the mixed bitumen product stream, at least two bitumen feed streams may be admixed. The bitumen feed streams may be or include, a virgin bitumen, a bitumen recycle stream, and combinations thereof. A bitumen recycle stream may be or include, but is not limited to, recycled asphalt recovered from roads or parking lots, recycled roofing shingles, recycle roofing membranes, and combinations thereof. This process stream has, in most embodiments, been melted and treated to remove fillers and other compositions such as gravel.

In some embodiments, a 'bitumen feed stream' may not even consist of bitumen. For example, a refinery may elect to use a heavy hydrocarbon that is not quite a bitumen as a diluent for an exceptionally heavy bitumen. In most embodiments though, the bitumen feed streams will be a recycled bitumen feed stream and a virgin bitumen feed stream.

In the practice of certain embodiments of the methods of the disclosure, the feed streams will be admixed to form a product stream. Any method of performing this function may be employed. For example, the feed streams may be introduced into a tank and agitated. In an alternative embodiment, the feed streams may be co-injected into a line having static mixers in place. In still another embodiment, both methods may be employed to mix bitumen feed streams to prepare a bitumen product stream.

In the practice of the methods of the disclosure, each feed stream and a resulting product stream is analyzed using the Bitumen Asphaltene Stability Index Test (BASIT) to determine an asphaltene stability index (ASI) value. The index values for the feed stream are then averaged weighted upon their proportion. For example, if there are only two feed streams and they are of the same volume, then the index values for each stream are then merely averaged. If the two streams were being used in a ratio of 2:1, then the index values would then also be weighted 2:1.

Once the average value for the feed streams is determined, it is then compared to the value for the bitumen product stream. There are three possibilities. One possibility is that average values are lower than that of the products stream. If the product stream has an ASI that is less than about 90% that of the average ASI for the feed streams, then it is likely that the product stream will be unstable and remedial efforts should be taken.

The other two possibilities are that the product steam ASI is equal to or greater than the average feed stream ASI. In these instances, the product stream will have a high probability of being stable.

In those embodiments of the method of the disclosure where the product stream has a too low ASI, then remedial efforts may be employed. At least one such remedial effort may be to use a stabilizing additive to produce a modified bitumen wherein the modified bitumen has a physical property change, as compared to the unmodified bitumen. The physical property may be selected from the group consisting of: a set up point or softening point that is at least 2° C. lower than the unmodified bitumen; an asphaltene stability that is improved such that asphaltenes are more resistant to precipitation during asphalt blending, gasoil blending, vacuum gasoil blending, storage and transport as compared to an unmodified bitumen; an improved resistance to oxidative aging; a more stable viscosity; an improved adhesive strength of wherein the modified bitumen has an adhesive strength that is at least 10 percent greater than unmodified bitumen; and combinations thereof.

Any additive known to be useful to those of ordinary skill in the art may be employed with the method of the disclosure. For example, in one embodiment, the additive is prepared from a formulation including: a first component selected from the group consisting of (alkoxylated)-(di or tri)-alkyl phenol-aldehyde (amine) resins; α-Olefin-maleic anhydride co-polymers and grafted polymers including half ester/amide and full ester/amide derivatives; and combinations thereof. The formulation also includes a second component which is a synergist and selected from the group consisting of polyamines, amidoamines, imidazolines, and combinations thereof.

For the purposes of the application, the term unstable when used regarding bitumen means that the subject bitumen has undesirable properties generally not apparent immediately after being prepared, but that develop over time both during and after storage. Bitumen is often obtained from vacuum tower bottoms or from visbreakers and then often combined with lighter streams such are gas oil to reduce the viscosity and improve handling properties. The asphaltenes in such bitumen can be unstable in themselves or may become unstable when blended with other streams such as gas oil or other bitumen. Unstable asphaltenes can lead to premature aging of the asphalt when it is applied as a final product, either as a pavement or in the roofing industry. The additives of the application may function to increase the stability of the bitumen by stabilizing the asphaltenes. In such embodiments, the additives are often employed at a concentration from about 0.01 to about 10 wt %.

Asphalt or bitumen can be easily oxidized. For example, it can be oxidized in as little as 4 hours by mixing the asphalt with air and heating to between about 179° C. and about 260° C. The additives can, in some embodiments, reduce such oxidation. Such a reduction may be measured in any way known to be useful to those of ordinary skill in the art. For example, oxygen uptake rates may be measures inside of pressurized vessels. Another example would be to measure changes in the acid number of the bitumen. Still other tests include, but are not limited to RTFOT (Rolling Thin Film Oven Test) and PAV (Pressure Aging Vessel).

When employed in applications such as road paving, it is important that bitumen have a good adhesion to the inorganic matrix used to extend the bitumen. For example, in some such applications, the adhesion between modified bitumen and gravel may be improved by at least 10 percent. In other embodiments, the adhesion may be increased by as much as 90% as compared to unmodified bitumen.

The viscosity of the bitumen itself may, in some embodiments of the method of the application, may be improved. As recovered from a refining process, at least some lots of bitumen may continue to have internal reactions that increase the viscosity of the bitumen. Some of this may be due to instable asphaltenes as discussed above, but asphaltenes are not the only compounds in bitumen that may continue to increase the viscosity. In some embodiments of the method of the application, the additives may be employed to stop or at least mitigate viscosity growth thereby preventing handling problems with aged bitumen.

In other embodiments, the additive is prepared from a formulation comprising: a first component selected from the group consisting of (alkoxylated)-(di or tri)-alkyl phenol-aldehyde (amine) resins; α-olefin-maleic anhydride co-polymers and grafted polymers including half ester/amide and full ester/amide derivatives; and combinations thereof; and a second component which is a synergist and selected from the group consisting of polyamines, amidoamines, imidazolines, and combinations thereof. Alkylphenol-formaldehyde resins are typically prepared by the acid or base catalyzed condensation of an alkylphenol with formaldehyde. Alkyl groups are straight or branched and contain about 3 to about 18, preferably about 4 to about 12 carbon atoms. Representative acid catalysts include dodecylbenzenesulfonic acid (DDBSA), toluene sulfonic acid, boron trifluoride, oxalic acid, and the like. Representative base catalysts include potassium hydroxide, sodium methoxide, sodium hydroxide, and the like. In an embodiment, the alkylphenol-formaldehyde resins have a molecular weight (Mn) of about 1,000 to about 50,000. In another embodiment, the alkylphenol-formaldehyde resins have a molecular weight of about 1,000 to about 10,000.

Alkylphenol-formaldehyde resins may be oxyalkylated by contacting the alkylphenol-formaldehyde resins with an epoxide such as ethylene oxide in the presence of a basic catalyst. For example, such resins may be prepared using sodium hydroxide or potassium hydroxide. The molar ratio of epoxide to OH group on the resin may be from about 1 to about 50. In some embodiments, the molar ratio is from about 2 to about 8. In still other embodiments, the molar ratio is from about 3 to about 7. The alkylphenol formaldehyde resins and oxyalkylated alkylphenol formaldehyde resins may be prepared using any method known to be useful to those of ordinary skill in the art of preparing such resins.

The resins may be prepared with ethylene oxide and/or propylene oxide. The alkyl groups may have from about 1 to about 30 carbons. Phenols useful include, but are not limited to phenol, cresol and resorcinol. Aldehydes include but are not limited to formaldehyde, acetaldehyde, propylaldehyde, and butyraldehyde and mixtures thereof. Amines, useful for Mannich resins may be selected from the any amine, but in some embodiments they may be selected from the group consisting of ethylene diamine, triethylene tetra-amine, tributyl tetra-amine, tetraethyl penta-amine, pentaethyl hexa-amine, hexaethyl hepta-amine, heptaethyl octa-amine, bis-hexamethytriamine, and mixtures thereof.

When the additive includes an α-olefin-maleic anhydride co-polymer and/or grafted polymer including half ester/amide and full ester/amide derivatives, they may be prepared admixing the monomers and using a catalyst or even heat to polymerize the monomers. Catalysts useful wither the method of the disclosure include, but are not limited to free radical initiator, organic peroxides, chromium catalysts, Ziegler-Natta catalysts and metallocene catalysts.

The additives useful with some embodiments of the invention may include other organic compounds and organic solvents. Organic compounds useful with some embodiments of the additives include, but are not limited to amines and esters. For example, a method of the invention may be practiced using additives including triethyl tetra-amine, tributyl tetra-amine, ethylene diamine, tetraethyl penta-amine, ethyl acetate, propyl acetate, ethyl butyrate, and the like and combinations thereof.

The synergists include polyamines, heavy polyamine, amidoamines, imidazolines, and combinations thereof. When the synergist is a polyamine, in some embodiments is may be selected from polymers of ethylene diamine, triethylene tetra-amine, tributyl tetra-amine, tetraethyl penta-amine, pentaethyl hexa-amine, hexaethyl hepta-amine, heptaethyl octa-amine, bis-hexamethytriamine, and mixtures thereof. The synergists may also be the quaternary ammonium salts of these compounds.

When the synergist is an amidoamines, in some embodiments, it may be a tall oil fatty acid amide prepared using one of ethylene diamine, triethylene tetra-amine, tributyl tetra-amine, tetraethyl penta-amine, pentaethyl hexa-amine, hexaethyl hepta-amine, heptaethyl octa-amine, bis-hexamethytriamine, and mixtures thereof. The synergists may also be the quaternary ammonium salts of these compounds.

When the synergist is an imidazoline, it may be prepared using a tall oil fatty acid-amidoamine and a polyamine and/or heavy polyamine as detailed above. It may be further substituted by forming alkyl esters, phosphate esters, thiophosphate esters, Tetra-propenyl succinic anhydride (TPSA), dodecylsuccinic anhydride, amides/esters alkylphosphate esters, arylphosphate esters along the backbone. The synergists may also be the quaternary ammonium salts of these compounds.

In employing such additives, their concentration in bitumen/asphalt in some application may be from about 0.01 to about 10% by weight. In other embodiments, the concentration may be from about 0.1 to about 0.5 weight %.

The organic solvents useful with some embodiments of the invention may include but are not limited to: ethyl benzene, xylene, toluene, and the like. When a solvent is present in the additive, it may be present at a concentration of from about 5 w/v percent to about 95 w/v percent. In other embodiments, the solvent if present at all is present at a concentration of from about 10 to 90 percent. In still other embodiments, the solvent may be present at a concentration of from about 15 to about 85 percent.

The additives disclosed herein may be used in any amount useful in lowering the set up point or softening point of a modified bitumen at least 2 degrees centigrade (2° C.) as compared to the same but unmodified bitumen. Set up point determinations may be made using any method known to those of ordinary skill in testing bitumen. For example, one such method that may be used includes stirring bitumen with a stir rod and noting the temperature wherein the stir rod becomes fixed and cannot be moved. Instrumental methods employing differential scanning calorimeters, for example, may also be employed.

Some of the components of the additives of the disclosure may have boiling points or vapor pressures that would cause those components to vaporize and be wasted if heated too quickly or under conditions that would not favor incorporation of those components into the bitumen. It follows then that when the bitumen is to be heated to a point near or above the boiling point of the additive component, the bitumen and additive are to be admixed first and then gradually heated to allow all, or as much as possible, of the additive component to be incorporated into the bitumen.

Embodiments of the methods of the application may be employed in any application where bitumen is being transported or moved and it would be desirable to avoid having to reheat the bitumen. For example, in one embodiment, bitumen is being transported in a rail or tank car and the rail car or tank begins to cool as soon as it is loaded. An additive of the invention is employed to lower the set up point sufficiently to allow the rail car or tank car to arrive at its destination before it has cooled to the set up point of the subject bitumen, thereby allowing the rail car or tank car to be off loaded without reheating. In another application, an additive of the invention is employed within a refinery to allow a bitumen that, unmodified, would be too viscous to move through a unit to be moved without the use of solvents or manual washouts. In still another embodiment, the additive is used to reduce the amount of energy necessary to pump a bitumen.

In addition to being a tool for determining whether or not a product bitumen admixture should be treated to mitigate instability, it may be desirable to use the method of the application to model the production process instead. In such embodiments, the materials to be used as bitumen feed streams are sampled prior to admixing them and then the samples are tested for ASI values. The samples are then admixed and the admixture tested for an ASI value. If the ASI value of the product stream is less than that of the average fees streams, then the streams can be admixed in different ratios or perhaps combined with different sources of bitumen.

EXAMPLES

The invention will now be illustrated with respect to certain Examples, which are not intended to limit the invention, but instead to more fully describe it.

FIG. 1 is a graph of the measured transmittance values per amount of non-solvent added to samples 1-6. Sample 1 is 100 vol % of a Western Canadian Select (WCS) bitumen; sample 2 is 90 vol % WCS bitumen and 10 vol % of a Bakken bitumen; sample 3 is 67 vol % WCS bitumen and 33 vol % Bakken bitumen; sample 4 is 33 vol % WCS bitumen and 67 vol % Bakken bitumen; sample 5 is 10 vol % WCS bitumen and 90 vol % Bakken bitumen; sample 6 is 100 vol % Bakken bitumen. Samples 1-6 all include 1 gram of its noted bitumen sample.

The inflection point value (IPV) for sample 1 occurs when about 1.8 mL of non-solvent is added; the IPV for sample 2 occurs when about 1.75 mL of non-solvent is added; the IPV for sample 3 occurs when about 1.38 mL of non-solvent is added; the IPV for sample 3 occurs when about 1.38 mL of non-solvent is added; the IPV for sample 4 occurs when about 0.75 mL of non-solvent is added; the IPV for sample 5 occurs when about 0.25 mL of non-solvent is added; the IPV for sample 6 occurs when about 0.13 mL of non-solvent is added.

As noted from FIG. 1, sample 1 would be considered the most stable sample, and sample 6 would be considered the least stable sample.

What is claimed is:

1. A method of preparing bitumen comprising:
   obtaining an inflection point value for a mixed bitumen product stream sample comprising at least two bitumen feed streams; wherein the inflection point value correlates to the stability of the mixed bitumen product stream based on the amount of added non-solvent; wherein the obtaining the inflection point value occurred by:
      adding a non-solvent to the mixed bitumen product stream sample;
      transmitting near IR laser light through the mixed bitumen product stream sample;
      determining an inflection point value that correlates to the stability of the mixed bitumen product stream based on the amount of non-solvent added; and
   modifying the mixed bitumen product stream when the inflection point value occurs at a ratio of less than about 2 mL of added non-solvent per 1 gram of the mixed bitumen product stream sample wherein the modifying the mixed bitumen product stream is selected from the group consisting of:
      altering the ratio of the at least two bitumen feed streams within the mixed bitumen product stream;
      introducing at least one stabilizing additive to the mixed bitumen product stream; and
      combinations thereof: and
   giving a result selected from the group consisting of:
      a stable mixed bitumen product stream;
      the mixed bitumen product stream having a viscosity less than an otherwise identical mixed bitumen feed stream absent the modifying the mixed bitumen product stream; and
      both;
   where the at least two bitumen feed streams are selected from the group consisting of:
      at least two bitumen feed streams where both bitumen feed streams comprises bitumen; and
      at least one bitumen feed stream comprising bitumen and at least one heavy hydrocarbon.

2. The method of claim 1, wherein the modifying the mixed bitumen product stream occurs when the ratio is less than about 1.2 mL of added non-solvent per 1 gram of the mixed bitumen product stream sample.

3. The method of claim 1, wherein the modifying the mixed bitumen product stream occurs by introducing the at least one stabilizing additive to the mixed bitumen product stream; and wherein the method further comprises analyzing the stability of the mixed bitumen product stream comprising the at least one stabilizing additive.

4. The method of claim 3, wherein the at least one stabilizing additive is prepared from a formulation including a first component selected from the group consisting of (alkoxylated)-(di or tri)-alkyl phenol-aldehyde (amine) resins;α-Olefin-maleic anhydride co-polymers and grafted polymers including half ester/amide and full ester/amide derivatives; and combinations thereof.

5. The method of claim 3, wherein the at least one stabilizing additive is prepared from a formulation including a second component selected from the group consisting of polyamines, amidoamines, imidazolines, and combinations thereof.

6. The method of claim 3, wherein the at least one stabilizing additive is introduced at a concentration ranging from about 0.1 to about 10 wt % based on the total mixed bitumen product stream.

7. The method of claim 1, wherein the method occurs within a refinery.

8. The method of claim 1 wherein at least one of the two bitumen feed streams is selected from the group consisting of a virgin bitumen stream, a recycled bitumen stream, and combinations thereof.

9. The method of claim 8, wherein the recycled bitumen stream is selected from the group consisting of recycled asphalt recovered from roads or parking lots, recycled roofing shingles, recycled roofing membranes, and combinations thereof.

10. The method of claim 8, wherein the recycled bitumen stream does not comprise fillers and gravel.

11. The method of claim 1, wherein the viscosity of the modified mixed bitumen feed stream is less than an otherwise identical mixed bitumen feed stream absent the modifying the mixed bitumen product stream.

12. The method of claim 1 further comprising transporting the modified mixed bitumen product stream.

13. A method of preparing bitumen comprising:
   obtaining an inflection point value for a mixed bitumen product stream sample comprising at least two bitumen feed streams; wherein the inflection point value correlates to the stability of the mixed bitumen product stream based on the amount of added non-solvent; wherein the obtaining the inflection point value occurred by:
      adding a non-solvent to the mixed bitumen product stream sample;

transmitting near IR laser light through the mixed bitumen product stream sample;
determining an inflection point value that correlates to the stability of the mixed bitumen product stream based on the amount of non-solvent added; and
introducing at least one stabilizing additive to the mixed bitumen product stream when the inflection point value occurs at a ratio of less than about 2 mL of added non-solvent per 1 gram of the mixed bitumen product stream sample;
giving a result selected from the group consisting of:
a stable mixed bitumen product stream;
the mixed bitumen product stream having a viscosity less than an otherwise identical mixed bitumen feed stream absent the modifying the mixed bitumen product stream; and
both;
where the at least two bitumen feed streams are selected from the group consisting of:
at least two bitumen feed streams where both bitumen feed streams comprises bitumen; and
at least one bitumen feed stream comprising bitumen and at least one heavy hydrocarbon.

14. The method of claim 13, wherein the modifying the mixed bitumen product stream occurs when the ratio is less than about 1.2 mL of added non-solvent per 1 gram of the mixed bitumen product stream sample.

15. The method of claim 13, further comprising altering the ratio of the at least two bitumen feed streams to prepare the mixed bitumen product stream.

16. A method of preparing bitumen comprising:
obtaining an equilibrated mixed bitumen product stream sample comprising at least two bitumen feed streams;
analyzing the stability of the equilibrated mixed bitumen product stream comprising:
adding a non-solvent to the equilibrated mixed bitumen product stream sample;
transmitting near IR laser light through the equilibrated mixed bitumen product stream sample;
determining an inflection point value that correlates to the stability of the mixed bitumen product stream based on the amount of non-solvent added; and
modifying the mixed bitumen product stream when the inflection point value occurs at a ratio of less than about 2 mL of added non-solvent per 1 gram of the mixed bitumen product stream sample wherein the modifying the mixed bitumen product stream is selected from the group consisting of:
altering the ratio of the at least two bitumen feed streams within the mixed bitumen product stream;
introducing at least one stabilizing additive to the mixed bitumen product stream; and
combinations thereof: and
giving a result selected from the group consisting of:
a stable mixed bitumen product stream;
the mixed bitumen product stream having a viscosity less than an otherwise identical mixed bitumen feed stream absent the modifying the mixed bitumen product stream; and
both;
where the at least two bitumen feed streams are selected from the group consisting of:
at least two bitumen feed streams where both bitumen feed streams comprises bitumen; and
at least one bitumen feed stream comprising bitumen and at least one heavy hydrocarbon.

17. The method of claim 16, wherein the at least one stabilizing additive is prepared from a formulation including a first component selected from the group consisting of (alkoxylated)-(di or tri)-alkyl phenol-aldehyde (amine) resins; α-Olefin-maleic anhydride co-polymers and grafted polymers including half ester/amide and full ester/amide derivatives; and combinations thereof.

18. The method of claim 16, wherein the at least one stabilizing additive is prepared from a formulation including a second component which is a synergist and selected from the group consisting of polyamines, amidoamines, imidazolines, and combinations thereof.

* * * * *